United States Patent [19]

Krueger et al.

[11] 3,959,361

[45] *May 25, 1976

[54] PROCESS OF PRODUCING AMINO METHYLENE PHOSPHONIC ACIDS

[75] Inventors: Friedrich Krueger, Edingen; Lieselotte Bauer, Bad Duerkheim; Walter Michel, Ilvesheim, all of Germany

[73] Assignee: Joh. A. Benckiser GmbH, Ludwigshafen, Germany

[ * ] Notice: The portion of the term of this patent subsequent to Mar. 12, 1991, has been disclaimed.

[22] Filed: Dec. 11, 1973

[21] Appl. No.: 423,689

Related U.S. Application Data

[62] Division of Ser. No. 125,857, March 18, 1971, Pat. No. 3,816,517.

[30] Foreign Application Priority Data

Mar. 20, 1970 Germany.......................... 2013371

[52] U.S. Cl. ............................................. 260/502.5
[51] Int. Cl.² ......................................... C07F 9/38

[58] Field of Search ................................. 260/502.5

[56] References Cited
UNITED STATES PATENTS

| | | | |
|---|---|---|---|
| 3,796,749 | 3/1974 | Krueger et al. .................. | 260/502.5 |
| 3,816,517 | 6/1974 | Krueger et al. .................. | 260/502.5 |

FOREIGN PATENTS OR APPLICATIONS

| | | | |
|---|---|---|---|
| 1,142,294 | 2/1969 | United Kingdom.............. | 260/502.5 |

*Primary Examiner*—Joseph E. Evans
*Attorney, Agent, or Firm*—Erich M. H. Radde

[57] ABSTRACT

Substantially pure amino methylene phosphonic acids, such as ethylene diamine tetra-(methylene phosphonic acid), nitrilo tris-(methylene phosphonic acid), and others are obtained in a high yield by reacting α-amino mono- or polycarboxylic acids which are substituted at their amino nitrogen atom, or their alkali metal salts with phosphorous acid and/or a phosphorus trihalogenide, preferably phosphorus trichloride in the presence or absence of an inert diluent.

13 Claims, No Drawings

PROCESS OF PRODUCING AMINO METHYLENE PHOSPHONIC ACIDS

This is a division of application Ser. No. 125,857, filed Mar. 18, 1971, now Pat. 3,816,517.

BACKGROUND OF THE INVENTION

1. Field Of The Invention

The present invention relates to an improved process of producing amino alkylene phosphonic acids and more particularly to a process of producing substantially pure, crystalline amino methylene phosphonic acids in a high yield.

2. Description Of The Prior Art

Heretofore amino methylene phosphonic acids have been prepared, for instance, by reacting amines with formaldehyde and a compound of the trivalent phosphorus, such as phosphorus acid, esters of phosphorous acid, or phosphorus trichloride according to the following equation:

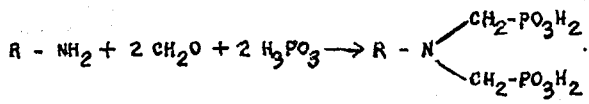

However, the yields obtained when proceeding according to this known process, are rather low and usually do not exceed about 55% to 60%. These low yields are due to the formation of oily by-products which are formed, for instance, on reacting ethylene diamine, formaldehyde, and phosphorus trichloride and which consist of ethylene diamine tri-(methylene phosphonic acids) and di-(methylene phosphonic acids) and other reaction products, and the separation of which from the resulting ethylene diamino tetra-(methylene phosphonic acid) is quite difficult.

SUMMARY OF THE INVENTION

It is one object of the present invention to provide an improved process of producing substantially pure, crystalline amino methylene phosphonic acids in a high yield substantially without the formation of oily by-products.

Other objects of the present invention and advantageous features thereof will become apparent as the description proceeds.

In principle the novel process of producing amino methylene phosphonic acids comprises reacting α-amino mono- and polycarboxylic acids which are substituted at their nitrogen atom or, respectively, their alkali metal salts with phosphorous acid and/or a phosphorous trihalogenide, preferably phosphorus trichloride in the presence or absence of an inert solvent. In said process the molar amount of the phosphorus compound is between 1 mole and 3 moles for each carboxyl group present in the α-amino mono- or polycarboxylic acid.

α-Amino mono- or polycarboxylic acids useful as the one reactant are, for instance, ethylene diamine tetraacetic acid, nitrilo triacetic acid, glycine bis-(methylene phosphonic acid), sarcosine monomethylene phosphonic acid, and others.

According to the process of this invention a reaction takes place between the carboxyl group of the one reactant and the phosphorus acid reactant or its derivative whereby the carboxyl group is replaced by a phosphonic acid group. For instance, the reaction between ethylene diamine tetraacetic acid and phosphorous acid proceeds according to the following equation whereby ethylene diamine tetra-(methylene phosphonic acid) is produced:

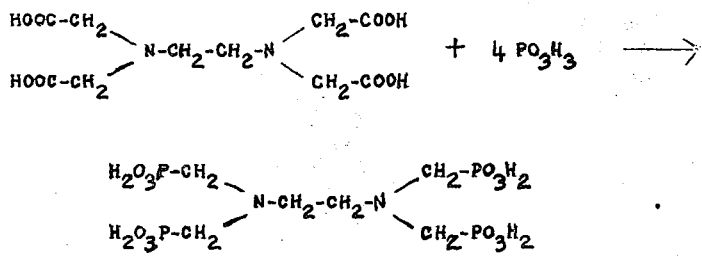

Nitrilo triacetic acid or glycine bis-(methylene phosphonic acid) yield nitrilo tris-(methylene phosphonic acid).

It was not known heretofore and is entirely unexpected that the carboxyl group can be replaced by the phosphonic acid group. On the contrary, as has been described in numerous patents, the carboxyl groups usually react with phosphorus trichloride or, respectively, with phosphorous acid in mixture with phosphorus trichloride, in an entirely different manner. For instance, according to the German published Application No. 1,148,235 unsubstituted mono- or dicarboxylic acids yield, on reaction with phosphorus trichloride, hydroxy alkyl diphosphorus trichloride, hydroxy alkyl diphosphoric acids according to the following equation:

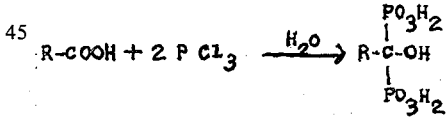

According to British Patent No. 1,129,687 phosphono acetic acid reacts with a mixture of phosphorus trichloride and phosphorous acid to yield ethane-1-hydroxy-1,1,2-triphosphonic acid. In contrast to the process described in German published Application No. 1,148,235 the reaction according to the above mentioned British Patent is carried out in an inert diluent in the absence of water.

According to A. Badinand et al. "Bull. Soc. Chem. France" vol. 1958, page 1495, attempts have been made to react ethylene diamine tetraacetic acid or nitrilo triacetic acid with phosphorus trichloride to produce the corresponding acid chlorides. These attempts, however, were unsuccessful. Only undefinable, gummy and tarry reaction products were obtained.

It is, therefore, highly unexpected and very surprising that, when proceeding according to the present invention and reacting ethylene diamine tetraacetic acid or nitrilo triacetic acid with a mixture of phosphorous acid and phosphorus trichloride, substantially crystalline amino methylene phosphonic acid are obtained, namely ethylene diamine tetra-(methylene phosphonic acid) or, respectively, nitrilo tris-(methylene phosphonic acid).

As stated above, the process according to the present invention has the advantage over the known process of producing, for instance, ethylene diamine tetra-(methylene phosphonic acid) or nitrilo tris-(methylene phosphonic acid) from the corresponding amines, formaldehyde, and phosphorus trichloride, that the amino methylene phosphonic acids are obtained in a considerably higher yield. For instance, the yield of ethylene diamine tetra-(methylene phosphonic acid) from ethylene diamine is between about 55% and 60%, while the yield of the same compound, when reacting ethylene diamine tetraacetic acid according to the present invention, amounts to about 80% to 85%.

For carrying out the process according to the present invention the α-amino carboxylic acid substituted at its amino nitrogen atom is suspended in an inert diluent. One half to one mole of phosphorous acid for each mole of carboxyl groups present in the starting material, is added thereto. Thereafter, one half to one mole of phosphorus trichloride is added drop by drop while stirring vigorously. The reaction mixture is then heated in the boiling water bath for several hours. Thereby, lively reaction and carbon dioxide development take place. The reaction mixture changes its color due to the formation of an orange colored by-product. Water is added and the reaction mixture is heated in the water bath for some time to complete the reaction. Decolorizing carbon is admixed. The yellow by-products are removed together with the charcoal by filtration by suction. The organic solvent layer is then separated and the aqueous layer is concentrated by evaporation in a vacuum and the phosphonic acid is obtained in pure form. If a phosphonic acid is formed which is difficultly soluble in water, it can be separated from the yellow by-products by dissolving the reaction product in a small amount of sodium hydroxide solution and adjusting the pH-value to a pH of 7.0. The pure phosphonic acid is precipitated by acidifying the aqueous solution of its sodium salt with hydrochloric acid.

It is, of course, also possible to change the order in which the reactants are mixed and reacted with each other. Thus part of the inert diluent, the phosphorous acid, and the phosphorus trichloride are mixed with each other and are heated in the boiling water bath while stirring. A suspension of the α-amino carboxylic acid in the remainder of the inert solvent is added drop by drop to said heated mixture. Thereupon the reaction proceeds as described above.

Tetrachloro ethane, trichloro ethylene, tetrachloro ethylene, carbon tetrachloride, o-chloro toluene, dichloro benzene, monochloro benzene, and other substantially inert aliphatic and aromatic halogenated hydrocarbons as well as aliphatic and aromatic hydrocarbons such as paraffin, toluene, and the like are especially useful inert diluents.

In place of a mixture of phosphorous acid and phosphorus trichloride, there can be employed phosphorus trichloride alone but with the required amount of water whereby it can be assumed that the water reacts with phosphorus trichloride to form phosphorous acid so that a mixture of phosphorous acid and phosphorus trichloride is present in the reaction mixture. Preferably phosphorus trichloride and water are added separately but at the same time to the suspension of the amino carboxylic acid in the inert diluent.

It is also possible to employ more than half of the phosphorus reactants in the form of phosphorus trichloride and correspondingly less of phosphorous acid and to compensate the deficit of phosphorous acid by the addition of water to react with the excess of phosphorus trichloride.

Furthermore, the reaction can also be carried out with phosphorous acid alone and in the absence of an inert solvent, whereby the reaction mixture must be heated to a temperature between 130°C. and 160°C., preferably at 140°C. Such a procedure has proved of value, for instance, when converting glycine bis-(methylene phosphonic acid) into nitrilo tris-(methylene phosphonic acid).

DESCRIPTION OF THE PREFERRED EMBODIMENTS

The following examples serve to illustrate the present invention without, however, limiting the same thereto.

Example 1

A suspension of 291 g. of ethylene diamine tetraacetic acid (1 mole) and 328 g. of phosphorous acid (4 moles) in 1000 ml. of chloro benzene is heated in the boiling water bath while stirring. 550 g. of phosphorus trichloride (4 moles) are slowly added drop by drop thereto. Heating of the mixture is continued for two more hours whereby lively carbon dioxide development sets in. The reaction mixture changes its color with the formation of a yellow by-product. 1000 ml. of water are added thereto and heating of the resulting mixture is continued for one more hour. After cooling, the resulting phosphonic acid precipitates together with the yellow byproducts. It is filtered off and the residue is brought into solution by means of an aqueous sodium hydroxide solution and adjusting the pH-value to a pH of 7.0. Decolorizing carbon is added to the solution which is then filtered by suction. Thereby the phosphonic acid is dissolved as sodium salt, while the by-products are removed by the treatment with the carbon. On adding the required amount of hydrochloric acid to the aqueous solution, pure ethylene diamine tetra-(methylene phosphonic acid) precipitates. It is filtered off and dried.

Yield: 84% of the theoretical yield.

The compound is identified as substantially pure phosphonic acid by chemical analysis.

Found: 16.18% C; 4.64% H; 6.03% N; 27.60% P.
Calculated: 16.51% C; 4.62% H; 6.43% N; 28.44% P.

Furthermore, its proton resonance spectrum proves that the reaction product is identical with ethylene diamine tetra-(methylene phosphonic acid).

Example 2

582 g. of ethylene diamine tetraacetic acid (2 moles) are suspended in 2000 ml. of chloro benzene. The suspension is heated in the boiling water bath while stirring. To said suspension there are added drop by drop separately but at the same time 2,192 g. of phosphorus trichloride (16 moles) and 432 g. of water (24 moles). Heating of the resulting mixture in the boiling water bath is continued for two or three hours. 2,000 ml. of water are added thereto, stirring of the reaction mixture is continued at 100°C. for one more hour, the mixture is cooled, and the precipitate is filtered off by suction.

The filter residue is dissolved in aqueous sodium hydroxide solution whereby the pH-value is adjusted to a pH of 7.0, decolorizing carbon is added, the carbon is filtered off by suction, and the aqueous filtrate is acidified with the required amount of hydrochloric acid. Thereby, substantially pure ethylene diamine tetra-(methylene phosphonic acid) is obtained in a yield of 80% of the theoretical yield.

Example 3

961 g. of phosphorus trichloride (7 moles) are slowly added drop by drop to a suspension of 291 g. of ethylene diamine tetraacetic acid (1 mole), 82 g. of phosphorous acid (1 mole), and 162 g. of water (9 moles) which suspension was previously heated to 100°C. in the boiling water bath. Thereafter, heating in the boiling water bath is continued for 3 more hours while stirring. 1000 ml. of water are added and the mixture is heated for one more hour. Aqueous sodium hydroxide solution is added to the reaction mixture until the pH-value of the solution is adjusted to a pH of 7.0. Decolorizing carbon is added to the resulting solution whereafter the mixture is filtered by suction. The aqueous layer of the filtrate is separated by means of a separating funnel from the organic solvent layer. The resulting ethylene diamine tetra-(methylene phosphonic acid) is precipitated from the aqueous solution of its sodium salt by the addition of the required amount of hydrochloric acid.
Yield: 80% of the theoretical yield.

Example 4

263 g. of glycine bis-(methylene phosphonic acid) and 164 g. of phosphorous acid are heated in a vacuum at an oil bath temperature of 140°C. for eight hours, while stirring. After cooling, the reaction mixture solidifies. To purify the reaction product, it is dissolved in 400 g. of water. Excess aniline dissolved in ethanol is added thereto. The aniline salt crystallizes and can be recrystallized from a mixture of ethanol and water (3 : 1).
Yield: 55% of the theoretical yield. The yield can be considerably improved by concentrating the filtrate by evaporation.

The aniline salt is suspended in water. Sodium hydroxide is added thereto. The aniline split off thereby is removed by shaking and extracting with chloroform. The alkaline solution is passed through a cation exchange column. The aqueous eluate which contains the free phosphonic acid is concentrated by evaporation in a vacuum. The resulting crude product is purified by dissolving it in water followed by precipitation with acetone.

The proton resonance spectrum of the resulting reaction product proves that it is identical with nitrilo tris-(methylene phosphonic acid) obtained according to conventional methods.

Example 5

191 g. of nitrilo tris-acetic acid (1 mole) and 328 g. of phosphorous acid (4 moles) are suspended in 1000 ml. of chloro benzene. The suspension is heated in the boiling water bath. 549 g. of phosphorus trichloride (4 moles) are added slowly drop by drop within 90 minutes. Stirring is continued for two more hours while heating in the boiling water bath. Thereby, vigorous carbon dioxide development takes place and the reaction mixture changes its color due to the formation of a yellow by-product. 1000 ml. of water are added to the mixture which is then heated for one more hour. Decolorizing carbon is added to the reaction mixture while still hot. The carbon is removed by filtration by suction together with the yellow by-product. The organic solvent layer is separated from the aqueous layer by means of a separating funnel and the aqueous layer is concentrated by evaporation in a vacuum. Thereby, a clear sirup is obtained. Said sirup is dissolved by boiling in 2,000 ml. of ethanol. Nitrilo tris-(methylene phosphonic acid) crystallizes on cooling.
Yield: 89.5% of the theoretical yield.

The proton resonance spectrum of the resulting reaction product proves that it is identical with nitrilo tris-(methylene phosphonic acid) obtained according to conventional methods.

Example 6

A suspension of 191 g. of nitrilo triacetic acid (1 mole) and 123 g. of phosphorous acid (1.5 moles) in 1000 ml. of tetrachloro ethane is heated to 100°C. in the boiling water bath. To said heated suspension there are added drop by drop 205.5 g. of phosphorus trichloride (1.5 moles) within 30 minutes while stirring. Stirring of the mixture in the boiling water bath is continued for three more hours. Thereafter, 1000 ml. of water are added to the reaction mixture and stirring is continued for one hour while heating. Decolorizing carbon is added to the reaction solution while still hot. After filtering off by suction the carbon and separating the organic solvent layer, the remaining aqueous layer is concentrated by evaporation in a vacuum. A clear sirup remains. It is dissolved in 2000 ml. of ethanol by boiling. On cooling, nitrilo tris-(methylene phosphonic acid) crystallizes.
Yield: 70% of the theoretical yield.

Example 7

137 g. of phosphorus trichloride (1 mole) are added slowly drop by drop to a suspension of 173 g. of sarcosine mono-(methylene phosphonic acid) and 82 g. of phosphorous acid (1 mole) in 1000 ml. of tetrachloro ethane while heating in the boiling water bath. Stirring and heating of the mixture are continued for 90 minutes. 1000 ml. of water are added thereto and the mixture is heated in the boiling water bath for one hour. The yellow by-product formed during the reaction is removed by the addition of decolorizing carbon and filtration. The organic solvent layer is separated from the aqueous layer which is then concentrated by evaporation in a vacuum. A sirupy residue is obtained thereby. It is dissolved in ethanol. Methylamino bis-(methylene phosphonic acid) precipitates gradually from the ethanol solution in crystalline form.
Yield: 82% of the theoretical yield.

In place of the α-amino carboxylic acid used as the one reactant in the process according to the present invention, there can be employed equimolecular amounts of other α-amino carboxylic acids. The preferred α-amino carboxylic acids, however, are those used as the one reactant in the preceding examples. Imino diacetic acid mono-(methylene phosphonic acid) of the formula

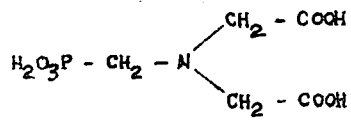

and polyalkylene amine polyacetic acids such as diethylene triamine pentaacetic acid can also be used.

Although the preferred reaction temperature is the temperature of the boiling water bath when operating in an inert diluent, it is also possible to operate at a temperature as low as 60°C. The upper temperature limit is that of the boiling point of the inert diluent used.

In place of phosphorus trichloride, there can also be used other phosphorus halogenides such as phosphorus tribromide or phosphorus triiodide, although phosphorus trichloride is the preferred reactant.

Preferred cation exchange resins used for purifying the salts of the resulting amino methylene phosphonic acids are the sulfonated polystyrene resins known to the art under the trademark "Duolite C 20". Other cation exchange resins can, of course, also be used.

The resulting amino methylene phosphonic acids are excellent complexing or sequestering agents for polyvalent metal ions, such as calcium, magnesium, iron, and the like ions. They are added, for instance, to fluid cleaning agents because they are stable against hydrolysis. They have become of greatly increased value during the last few years because they have proved to be effective even when employed in sub-stoichiometric amounts.

We claim:

1. A process for the preparation of an amino-methylene phosphonic acid comprising the steps of reacting a mixture consisting of an α-amino carboxylic acid compound selected from the group consisting of ethylene diamine tetraacetic acid, nitrilo triacetic acid, glycine bis-(methylene phosphonic acid), sarcosine mono-(methylene phosphonic acid), diethylene triamine pentaacetic acid, imino diacetic acid mono-(methylene phosphonic acid) and the alkali metal salts thereof, from about 1 mole to 3 moles based on each mole of carboxyl groups present in said alpha-amino carboxylic acid compound of a phosphorus source selected from the group consisting of (a) a mixture of phosphorous acid and a phosphorus trihalide selected from the group consisting of phosphorus trichloride, phosphorus tribromide and phosphorus triiodide, and (b) a mixture of said phosphorus trihalide and an amount of water sufficient to react therewith to produce a mixture of phosphorous acid and said phosphorus trihalide, and an inert organic diluent selected from the group consisting of tetrachloro ethane, trichloro ethylene, tetrachloro ethylene, carbon tetrachloride, o-chloro toluene, dichloro benzene, monochloro benzene, paraffin and toluene at an elevated temperature between 60°C. and the boiling point of said organic diluent, whereby the carboxylic acid groups are replaced by phosphonic groups, and thereafter recovering the resulting amino methylene phosphonic acid compound from the reaction mixture.

2. The process as defined by claim 1, wherein said temperature is the temperature of a boiling water bath.

3. The process as defined by claim 1, wherein said reaction conditions comprise suspending said alpha-amino carboxylic acid compound in said inert diluent and slowly adding thereto said phosphorus source while agitating the reaction mixture.

4. The process as defined by claim 3, wherein said reaction conditions further comprise the steps of continuing said agitation until the development of gaseous byproduct has ceased and thereafter adding water while continuing said elevated temperature conditions to complete the reaction.

5. The process as defined by claim 1, wherein said phosphorus source is a mixture of phosphorous acid and phosphorus trichloride.

6. The process as defined by claim 1, wherein said phosphorus is said mixture of phosphorus trichloride and water.

7. The process as defined by claim 6, wherein said reaction conditions comprise the steps of suspending said alpha-amino carboxylic acid compound and said phosphorous acid in the inert organic diluent, heating said suspension to said elevated temperature conditions and slowly adding said phosphorus trihalide with agitation.

8. The process as defined by claim 7, wherein said reaction conditions further comprise the steps of maintaining the reaction mixture at said elevated temperature until the development of gaseous byproducts ceases and thereafter adding water to the reaction mixture while maintaining said elevated temperature conditions to complete the reaction.

9. The process as defined by claim 1, wherein said phosphorus trihalide is phosphorus trichloride.

10. The process as defined by claim 1, wherein said alpha-amino carboxylic acid is ethylene diamine tetraacetic acid.

11. The process as defined by claim 1, wherein said alpha-amino carboxylic acid is nitrilo triacetic acid.

12. The process for the preparation of amino methylene phosphonic acids which comprises the steps of reacting a mixture consisting of an alpha-amino carboxylic acid compound selected from the group consisting of ethylene diamine tetraacetic acid, nitrilo triacetic acid, glycine bis-(methylene phosphonic acid), sarcosine mono-(methylene phosphonic acid), diethylene triamine pentaacetic acid, imino diacetic acid mono-(methylene phosphonic acid) and the alkali metal salts thereof, and from about 1 to 3 moles based upon each mole of carboxylic groups present in said alpha-amino carboxylic acid compound of a phosphorus compound which is a mixture of phosphorous acid and a phosphorus trihalide selected from the group consisting of phosphorus trichloride, phosphorus tribromide and phosphorus triiodide at an elevated temperature of 100°C., whereupon the carboxylic acid groups are replaced by phosphonic acid groups, and thereafter recovering the resulting amino methylene phosphonic acid compound from the reaction mixture.

13. The process as defined by claim 12, wherein said alpha-amino carboxylic acid is ethylene diamine tetracarboxylic acid.

* * * * *